United States Patent [19]
Freeman

[11] Patent Number: 5,403,554
[45] Date of Patent: Apr. 4, 1995

[54] APPARATUS FOR DEPOSITING FLUIDS ON A CHROMATOGRAPHY PLATE

[76] Inventor: Michael J. Freeman, 3390 Landings Dr., Ann Arbor, Mich. 48103

[21] Appl. No.: 261,752

[22] Filed: Jun. 17, 1994

Related U.S. Application Data

[63] Continuation of Ser. No. 51,751, Apr. 22, 1993, abandoned.

[51] Int. Cl.⁶ .................................................. B01L 3/02
[52] U.S. Cl. .................................... 422/100; 422/99; 73/863.32
[58] Field of Search .................. 422/68, 79, 99, 100; 73/864.21, 864.17, 863.32, 863.23

[56] References Cited

U.S. PATENT DOCUMENTS

| | | | |
|---|---|---|---|
| 2,764,980 | 10/1956 | Smith | 604/154 |
| 2,786,468 | 3/1957 | Singer et al. | 604/155 |
| 3,884,081 | 5/1975 | Griffith | 73/863.31 |
| 3,902,852 | 9/1975 | Lemieux et al. | 73/863.32 |
| 4,288,206 | 9/1981 | Tigwell et al. | 417/517 |
| 4,407,659 | 10/1983 | Adam | 604/155 |
| 4,827,780 | 5/1989 | Sarrine et al. | 73/864.21 |
| 4,846,797 | 7/1989 | Howson et al. | 604/154 |
| 4,931,041 | 6/1990 | Faeser | 604/155 |
| 5,021,217 | 6/1991 | Oshikubo | 422/100 |
| 5,055,271 | 10/1991 | Golias et al. | 422/99 |

OTHER PUBLICATIONS

Handbook of thin-layer chromatography, Copyright 1991, New York, N.Y., pp. 118-120.
Thin-Layer Chromatography, B. Fried & J. Sherma, Copyright 1986, New York, N.Y., pp. 66-78.

*Primary Examiner*—James C. Housel
*Assistant Examiner*—Rachel Heather Freed
*Attorney, Agent, or Firm*—Brooks & Kushman

[57] ABSTRACT

An apparatus for depositing fluids on a thin-layer chromatography plate is disclosed. The apparatus includes a housing for multiple syringes containing chromatography samples. The apparatus also includes an actuator for independently engaging the syringes to release those samples onto the thin-layer chromatography plate. The apparatus further includes a moveable platform for supporting the thin-layer chromatography plate in proximity to the syringes.

10 Claims, 3 Drawing Sheets

APPARATUS FOR DEPOSITING FLUIDS ON A CHROMATOGRAPHY PLATE

CROSS REFERENCE TO RELATED APPLICATION

This application is a continuation of United States patent application Ser. No. 08/051,751, filed Apr. 22, 1993, entitled "Apparatus for Depositing Fluids on a Chromatography Plate", now abandoned.

TECHNICAL FIELD

This invention relates generally to fluid application devices. More specifically, this invention relates to an apparatus for depositing fluids on a thin-layer chromatography plate.

BACKGROUND ART

Chromatography is a method of chemical analysis based upon the principles of phase distribution that uses differences in a variety of molecular properties to separate chemical compounds. Chromatography systems consist of a mobile phase and a stationary phase, where components of the sample to be separated are carried with varying migration rates by the mobile phase as it flows through the stationary phase. The more securely a component of the sample is held by the stationary phase, the higher the percentage of molecules of that component that will be held immobile. In contrast, a less securely held component will provide a higher percentage of molecules moving with the mobile phase. On average, the molecules of a less securely held component will move over the stationary phase, in the direction of flow, at a higher rate than the molecules of a more securely held component. As a result, components in the sample will tend to migrate into separate regions, or bands, of the stationary phase.

A number of different types of chromatography are well known including column chromatography thin-layer chromatography, gas chromatography and paper chromatography. Thin-layer chromatography (TLC), is characterized by a liquid mobile phase and a thin stationary phase which is supported by a rigid glass, plastic, or metal plate. TLC is performed by depositing a sample, which is dissolved in a volatile solvent, at the bottom of a TLC plate using a pipet or syringe in either a spot or line application. The solvent evaporates in the process, leaving the sample on the stationary phase. The plate is then subjected to a development process which separates components of the sample for identification.

For proper results, care is required in depositing samples on the TLC plate. The plate itself must be held substantially horizontally to prevent run-off of samples deposited thereon. Additionally, the syringe or pipet used for depositing the sample is typically held at an angle between zero and 45 degrees for optimum accuracy.

More importantly, however, the size of the sample deposited on the chromatography plate is limited by the type and thickness of the stationary phase coated on the plate. This is particularly critical in spot application of samples. In line application, the sample must also be deposited evenly. Line application of a sample is typically accomplished by manually moving the syringe or pipet linearly in a direction substantially perpendicular to the direction of mobile phase flow desired for the sample. In both spot and line applications, resolution is determined primarily by the size of the sample applied.

To obtain the best resolution with TLC, the sample is typically applied as a small spot of 1 mm or 2 mm diameter or in a thin line of similar width. This is usually accomplished by applying several small spots on top of each other or in a line. Moreover, in the process, the solvent must be allowed to completely evaporate before additional sample spots are applied at a given location.

As a result, an experienced technician is typically required to effect the application of samples to a TLC plate. Moreover, even an experienced technician can generally perform only one application at a time. The number of applications that can be performed in a given time is therefore limited.

A number of mechanical devices are known for fluid application generally. U.S. Pat. Nos. 2,764,980 issued to Smith, 2,786,468 issued to Singer et al and 4,846,797 issued to Howson et al disclose machines for injecting small quantities of liquid into living organisms. The machines include multiple housings and syringes. Multiple syringe plunger actuators can be driven either simultaneously or independently.

U.S. Pat. No. 4,288,206 issued to Tigwell et al discloses an automatic multiple water sampler including a stationary housing adapted to receive multiple syringes and a cam for simultaneously engaging or disengaging the syringe plungers. U.S. Pat. No. 4,931,041 issued to Faeser discloses an infusion syringe pump including a syringe housing adapted to receive a single syringe. A linearly moveable drive member actuates the syringe plunger and is also part of a control system used to determine the absolute plunger position.

The above noted devices, however, are not designed for fluid application in TLC. Specifically, these devices are not designed for use in conjunction with a TLC plate and therefore are unable to accurately apply samples to such a plate. This is particularly true with respect to line application.

U.S. Pat. No. 4,407,659 issued to Adam discloses a drive system for depositing samples for chemical analysis. The system includes a single syringe housing adapted to receive a syringe and a coupling block adapted to engage or retract the syringe plunger. The device, however, is not specifically designed for accurately depositing samples onto a TLC plate. Significantly, the device lacks the ability to effect line application of samples and does not overcome the problem of a limited number of samples that may be applied in a given time.

U.S. Pat. No. 5,055,271 issued to Golias et al discloses a pump inserter for test tubes. The device is relevant to the extent that it discloses a vertically moveable frame for inserting and retracting pump mechanisms into closed test tubes and a horizontally moveable frame for positioning the test tubes beneath the pump mechanisms.

There are also several commercial products designed to mechanically augment the process of depositing samples on a TLC plate. Most such systems utilize only a single syringe or pipet and therefore do not overcome the problem of a limited number of samples that can be applied in a given time. Moreover, none of these systems are capable of effecting both line and spot applications with multiple syringes or pipettes.

Other automated systems for depositing samples on a TLC plate spot fluid from a plurality of syringes but provide no mechanism for line application. Such systems also have no provisions for automatically cleaning the syringes and, if a single syringe happens to jam, the plating of the remaining syringes will cease until the jammed syringe is removed. These systems also are not designed to precisely deliver small volumes necessary for high performance analytical TLC.

The apparatus of the present invention has the control and accuracy of the best commercially available spotting units in a multiple syringe platform and allows for both line and spot application. The apparatus further allows for easy syringe cleaning after use, has special provision for syringe jamming, has a simple manual override mechanism, and is relatively inexpensive to produce. A wide range of sample volumes can be plated in spot or line geometry with a wide variety of syringes.

SUMMARY OF THE INVENTION

Accordingly, it is a principle object of this invention to provide an apparatus for depositing fluids on a TLC plate that provides for independent application of multiple samples.

Another object of this invention is to provide an apparatus for depositing fluids on a TLC plate that allows for either spot or line application of samples.

Yet another object of this invention is to provide an apparatus for depositing fluids on a TLC plate that allows for automatic release of inoperative syringes.

Still another object of this invention is to provide an apparatus for depositing fluids on a TLC plate that improves efficiency of sample application.

It is a further object of this invention to provide an apparatus for depositing fluids on a TLC plate that retracts the syringe plungers and provides for easy cleaning thereof.

A still further object of this invention is to provide an apparatus for depositing fluids on a TLC plate that is simple in design and inexpensive to manufacture.

In accordance with the foregoing objects, an apparatus for depositing fluids on a TLC plate is disclosed comprising housing means for receiving and housing a plurality of syringes. The apparatus further comprises actuator means mountable to selected syringes for independently engaging and actuating the selected syringes and releasing selected fluids therefrom onto the TLC plate. Finally, the apparatus also comprises moveable support means proximate the housing means for receiving and supporting the TLC plate.

The above-described objects and advantages, and others, will be apparent after consideration of the following detailed description in connection with the accompanying drawings.

DETAILED DESCRIPTION OF THE INVENTION

Figure 1:
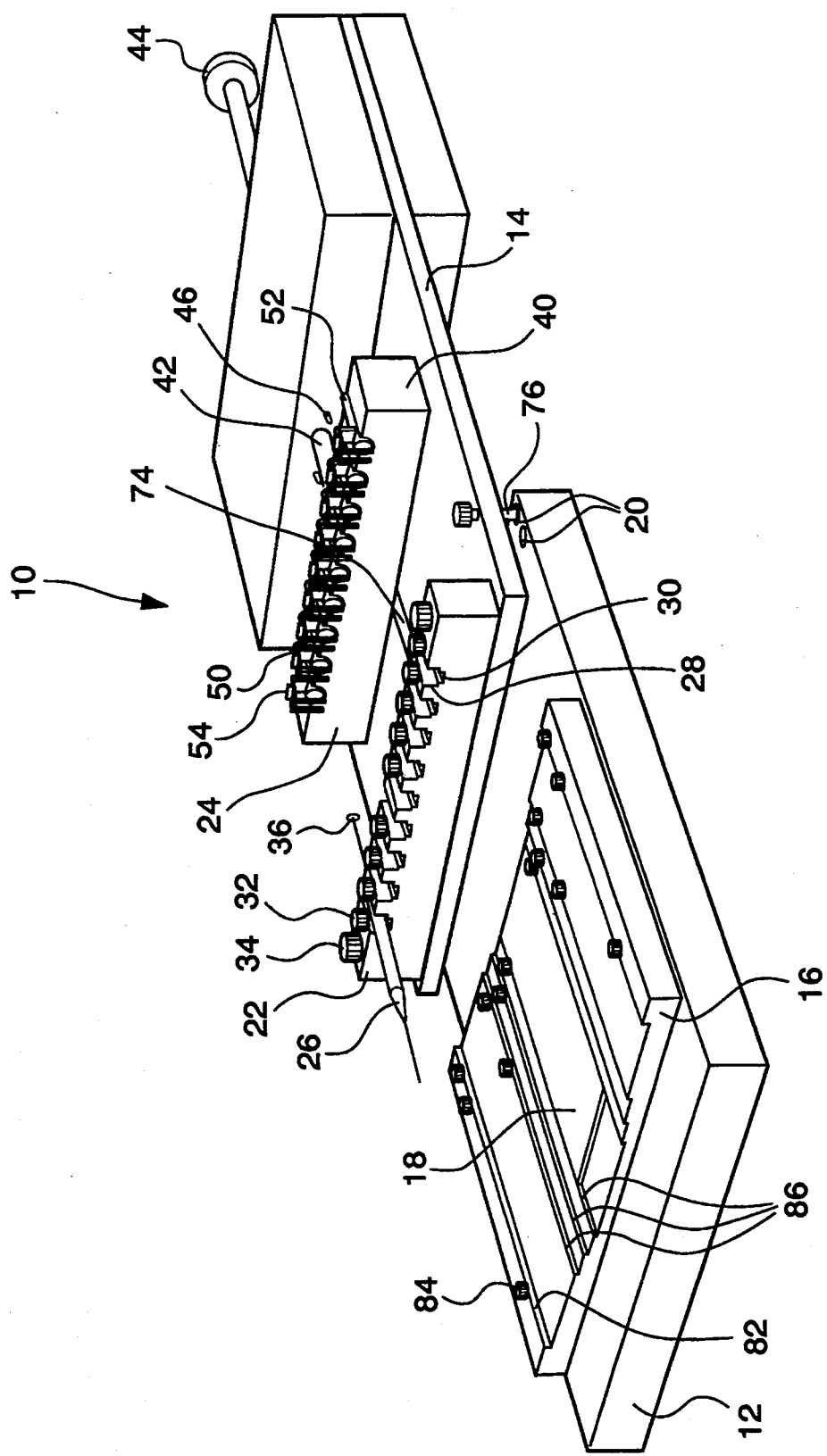
FIG. 1 is a perspective view of the apparatus for depositing fluids on a TLC plate of the present invention.
Figure 2:
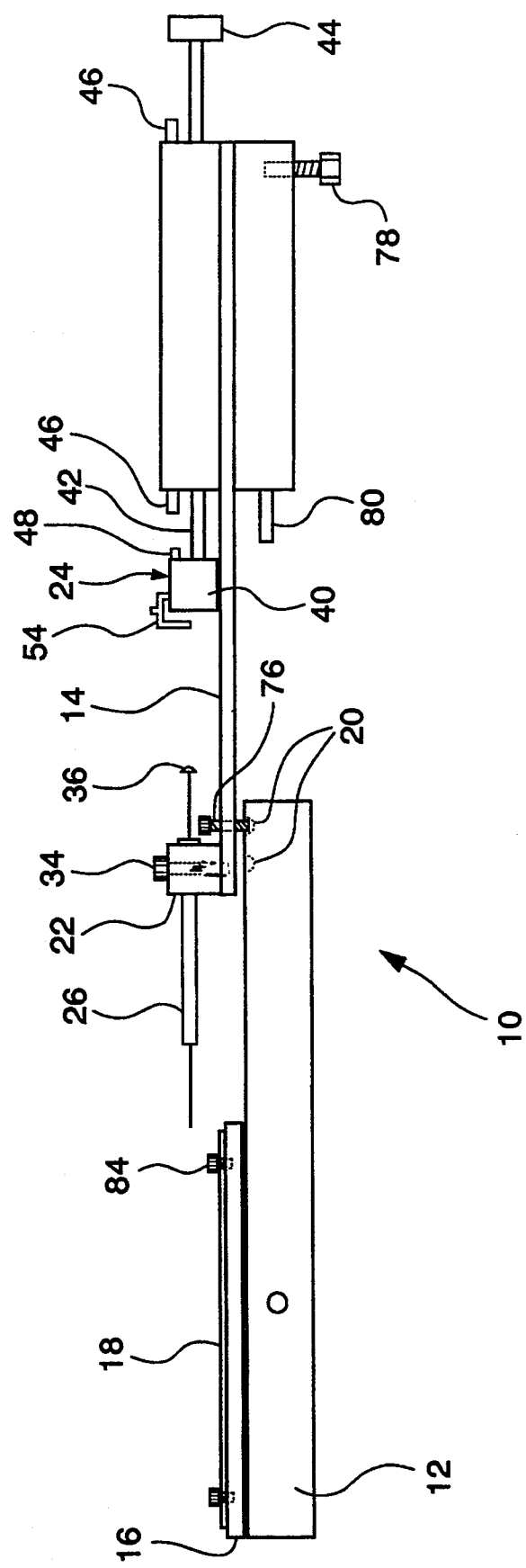
FIG. 2 is a side view of the apparatus for depositing fluids on a TLC plate of the present invention.
Figure 3:
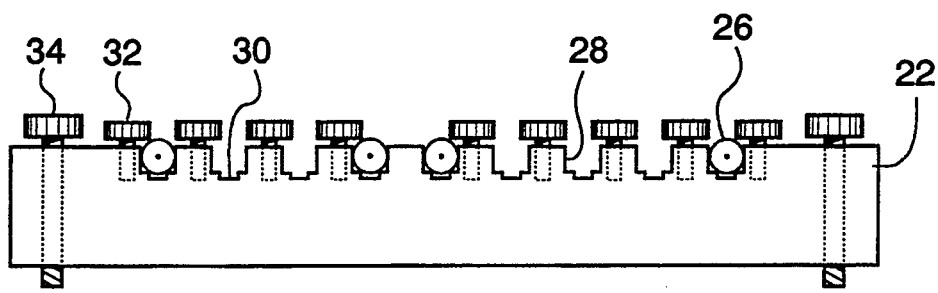
FIG. 3 is a front view of the housing of the apparatus for depositing fluids on a TLC plate of the present invention.

Referring now to FIGS. 1 through 3, the apparatus for depositing fluids on a TLC plate of the present invention is depicted generally by reference numeral 10. In its preferred embodiment, the apparatus 10 comprises a base 12 and a frame 14.

The base 12 includes a platform 16. Platform 16 provides support means for receiving and supporting a TLC plate 18. The base 12 also includes several pairs of indentations 20. As discussed in greater detail below, indentations 20 are provided to aid in the proper alignment of the base 12 and frame 14.

The frame 14 includes a housing 22 and an actuator 24. Housing 22 provides housing means for receiving and housing a plurality of syringes 26. Housing 22 is provided with a plurality of syringe grooves 28 and sub-grooves 30 adapted to receive the plurality of syringes 26. Grooves 28 and sub-grooves 30 are preferably adapted to orient the syringes 26 such that the longitudinal axes of the syringes 26 are substantially parallel. Each of the plurality of grooves 28 is provided with a thumb screw 32. The thumb screw 32 can be tightened to grippingly engage corresponding syringes 26, and form a stable three-way mount with the corners of the sub-grooves 30. By removing a thumb screw 32, the corresponding syringe 26 can easily be removed independent of other syringes 26. This allows for convenient removal of jammed syringes 26.

Housing 22 also includes a pair of mounting screws 34. The mounting screws 34 are provided to removably mount the housing 22 to the frame 14. Removal of the housing 22 from frame 14 allows for quick and easy loading and unloading of the plurality of syringes 26 from the apparatus 10 of the present invention. This allows two or more housings 22, each loaded with a plurality of corresponding syringes 26, to be used with the frame 14. While samples in one housing 22 are being applied, syringes 26 in another housing 22 are filled with the next set of samples to be used. A quick exchange of housings 22 allows nearly uninterrupted operation, reducing the overall time needed to apply a large number of samples.

Referring now to FIGS. 1 and 2, frame 14 also includes actuator 24. Actuator 24 provides actuator means for engaging and actuating the syringes 26 via corresponding syringe plungers 36. To this end, actuator 24 comprises a drive member 40 and a gear rack 42 driven by drive means such as an electric motor or the like (not shown). Drive member 40 is driven in a direction of motion that is substantially parallel to the longitudinal axes of the plurality of syringes 26 in either a forward or reverse direction.

Actuator 24 is preferably provided with an override handle 44 and limit switches 46. Override handle 44 facilitates manual adjustment of the position of the drive member 40. Limit switches 46 are operative to reverse the direction of motion of the drive member 40 at the extreme ends of the range of motion of the drive member 40. To this end, limit switches 46 are positioned to contact limit switch activation screws 48 on the drive member 40 and the override handle 44 as either approaches the electric motor. The limit switch activation screws 48 allow maximum backward draw of syringe plungers 36 during cleaning, and for adjustment for syringes 26 of varying sizes.

Figure 4:
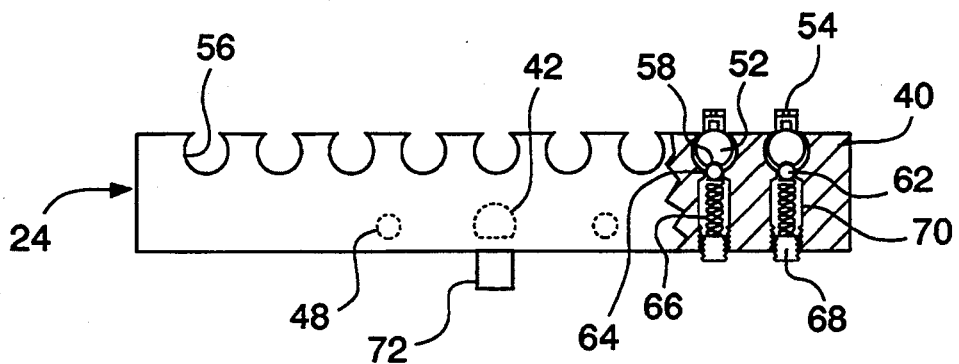
FIG. 4 is a front view in partial cross-section of the drive member of the apparatus for depositing fluids on a TLC plate of the present invention.
Figure 5:
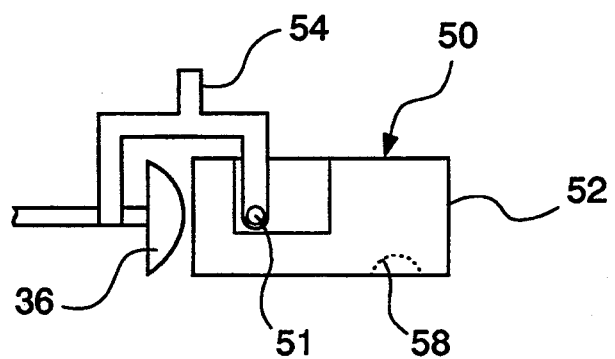
FIG. 5 is a side view of the coupling of the apparatus for depositing fluids on a TLC plate of the present invention.

Referring now to FIGS. 4 and 5, drive member 40 is provided with a plurality of couplings 50. Each coupling comprises a substantially cylindrical body 52 formed from a low friction material such as Delrin (acetal) or the like. The plurality of couplings 50 fit slidingly in a plurality of grooves 56 provided in drive member 40. The grooves 56 having longitudinal axes substantially coaxial with the longitudinal axes of the plurality of syringes 26. In the preferred embodiment, the material of drive member 40 into which grooves 56 are cut should also be low friction such as Delrin (acetal) or the like.

A pivotable attachment 54 is connected to the body 52 of each coupling 50 at a pivot point 51 in such a way that it can pivot between two useful positions. Attachments 54 are provided with an up position in which the coupling bodies 52 alone contact syringe plungers 36 from the back. The up position of attachments 54 allows application of varying initial sample sizes and allows retraction of drive member 40 without retraction of syringe plungers 36. Attachments 54 are also provided with a down position in which the coupling bodies 52 contact the syringe plungers 36 from the back, while attachments 54 removably engage the syringe plungers 36 from the front. This allows drive member 40 to engage and retract the syringe plungers 36, as is necessary for cleaning.

During operation, coupling bodies 52 engage syringe plungers 36 in the forward drive direction. Each coupling 50 is prevented from sliding freely in its corresponding groove 56 by the action of an indentation 58 in coupling body 52 and a protruding member 62 such as a spherical ball or the like, which extends into the indentation 58. The protruding member 62 is prevented from overextending into indentation 58 by a restraining ledge 64, but is free to move in the opposite direction. A variable force applied by a spring 66 and set screw 68 hold the protruding member 62 against the restraining ledge 64 unless a sufficient force is applied in the opposite direction. Each set screw 68, spring 66, and protruding member 62 occupy a hole 70 which is only slightly larger than each of the components, forcing them into a co-linear alignment.

A force acting on coupling 50 in a direction substantially parallel to its groove 56 is resisted by the force exerted by the corresponding spring 66, neglecting friction. Forces up to a magnitude determined by the compression force on spring 66 would not cause substantial motion of coupling 50 relative to drive member 40. Forces larger than this critical force, however, will exceed the ability of the spring 66 to resist them and will produce motion of the coupling 50 in its corresponding groove 56 relative to drive member 40. This configuration limits the force that can be applied by a coupling 50 to a syringe 26 that has jammed to a level determined by the compression force of the corresponding spring 66. In turn, the level of the compression force of the spring 66 is easily adjustable by means of set screw 68. A jammed syringe 26 will thus push or pull its corresponding coupling 50 all the way out of its groove 56. By loosening its corresponding thumb screw 32, the jammed syringe 26 can be easily removed from the top of housing 22 via groove 28. This also allows for uninterrupted sample application from the syringes 26 which do not jam. Thus, as is readily apparent, indentation 58, protruding member 62, restraining ledge 64, spring 66, set screw 68 and hole 70 together provide a release mechanism to halt actuation of a syringe plunger 36 in the event a syringe 26 jams.

As shown in FIGS. 1 and 4, drive member 40 is also provided with a flange 72. The flange 72 cooperates with a corresponding groove 74 in frame 14 to guide drive member 40 during operation. Specifically, flange 72 and groove 74 prevent deviations in the position of drive member 40 in a direction perpendicular to the desired direction of movement and also prevent angular deviations of drive member 40.

Referring again to FIGS. 1 and 2, frame 14 also includes a pair of front legs 76 and a rear leg 78. Front legs 76 seat in the indentations 20 of the base 12 previously described. In such a manner, front legs 76 cooperate with indentations 20 to accurately position the frame 14 relative to the base 12. As a result, front legs 76 and indentations 20 also accurately position the plurality of syringes 26 to the TLC plate 18, which are fixed relative to the frame 14 and base 12 via housing 22 and platform 16, respectively. Several sets of indentations 20, with various distances to platform 16, are provided to allow convenient positioning for a variety of syringe sizes. For each distance there are four indentations 20 which allow two lateral positions of the frame 14 relative to the base 12. These two positions are separated by half the distance between the syringes 26 in housing 22, allowing twice as many positions on a plate as there are syringes 26 to be easily accessed. Front and rear legs, 76 and 78, are also adjustable to change the height of the frame 14 over the base 12, thereby precisely orienting the syringes 26 at an optimum angle between zero and 45 degrees for depositing fluids on the TLC plate 18.

As shown in FIG. 2, frame 14 further includes cleaning post 80. Cleaning post 80 permits the frame 14 to be conveniently mounted to a separate cleaning stand (not shown) such that the longitudinal axes of the syringes 26 are oriented substantially vertically. Such an orientation, together with manual operation of actuator 24 via override handle 44 or high speed motorized operation, allows for quick and easy cleaning of the syringes 26 after operation of the apparatus 10 of the present invention.

Referring again to FIG. 1, base 12 includes moveable platform 16 for receiving and holding TLC plate 18. Platform 16 provides moveable support means for TLC plate 18 and serves to move the plate 18 back and forth in a direction of motion substantially perpendicular to the longitudinal axes of the plurality of syringes 26. To this end, platform 16 is provided with ledges 82 and thumb screws 84 to securely hold a plate 18 during such movement. Specifically, ledges 82 prevent the TLC plate 18 from sliding in the direction of motion of the platform 16 during operation of the apparatus 10. Thumb screws 84 are preferably formed of plastic and engage the surface of the plate 18. As with ledges 82, thumb screws 84 also aid in preventing sliding of the plate 18 during operation of the apparatus 10. However, thumb screws 84 also prevent any deviations in the position of the plate 18 in a direction perpendicular to the desired direction of motion. A series of sub-ledges 86 and thumb screws 84 allow the base 12 to be used with all standard sized TLC plates. Smaller plates are held in a way analogous to that used for the larger plate described above, but utilize the appropriate sub-ledges 86 and thumb screws 84 for the plate 18 to be held.

Referring again to FIGS. 1 and 2, during operation of the apparatus 10 of the present invention, the plurality of syringes 26 containing samples dissolved in a volatile liquid solvent are loaded into housing 22 and syringe plungers 36 are positioned in contact with couplings 50. Drive member 40 and gear rack 42 are driven such that couplings 50 engage syringe plungers 36 thereby discharging samples from the syringes 26 onto the TLC plate 18. Such multiple application of samples onto plate 18 increases the number of applications that can be performed in a given time, thereby increasing overall efficiency.

For proper operation of the apparatus 10, the electric motor driving actuator 24 should be of a type whose speed can be variably set at precisely controlled rates. Such control permits precisely calibrated volumes of liquid samples to be deposited on the TLC plate 18, in either line or spot applications, thereby improving overall chromatography results. To this end, the electric motor is preferably a programmable stepper motor, or any equivalent motor well known in the art. The speed of the electric motor and the rate of discharge of liquid samples from syringes 26 is set depending on the solvent used, the thickness, and the type of stationary phase coating on the TLC plate 18. The rate of discharge is also affected by whether or not any means of increasing the solvent evaporation rate, such as warm air flow or dry nitrogen flow, are used. While the preferred embodiment of the apparatus 10 does not contain such features, they can be easily added.

As previously described, during operation of the apparatus 10, samples are deposited from the syringes 26 onto the TLC plate 18. To this end, plate 18 is loaded onto platform 16 between ledges 82 and under thumb screws 84. Platform 16 holds plate 18 in a substantially horizontal orientation, thereby preventing run-off of the liquid samples deposited thereon.

As shown in FIG. 1, platform 16 is driven back and forth during operation of the apparatus 10 in an oscillating fashion via platform drive means such as a second electric motor or the like (not shown), thereby allowing for line application of the samples from the syringes 26 onto the plate 18. Once again, the electric motor should be of a type whose speed can be variably set at precisely controlled rates. Such control permits even deposit of samples to the TLC plate 18 during line applications, again providing for improved overall chromatography results. To this end, the electric motor is once again preferably a programmable stepper motor, or any equivalent motor well known in the art. The oscillating motion of the motor can be conveniently controlled through well known mechanical or electronic means to provide for variable line application lengths.

Additionally, the oscillating motion of the platform 16 can be conveniently disabled. Such an arrangement allows for spot application of samples from syringes 26 onto plate 18. Moreover, for improved precision in the line application of samples from syringes 26 onto plate 18, the electric motors driving actuator 24 and platform 16 are preferably electronically synchronized. Once again, such improved precision also improves overall chromatography results.

For maximum flexibility and accuracy of motion, the electric motors driving actuator 24 and platform 16 are preferably stepper motors with computer controlled microstepping drives. This configuration allows precise positioning and very small position increments without sacrificing high speed operation characteristics which are important for syringe 26 cleaning. This type of drive and separate computer control system is well known in the motion control field and thus is not presented here.

Thus, it is apparent that there has been provided, in accordance with the invention, an apparatus for depositing fluids onto a TLC plate which fully satisfies the objects and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the following claims.

What is claimed:

1. An apparatus for depositing fluids from a plurality of substantially parallel syringes onto a thin-layer chromatography plate, the apparatus comprising:
   a base;
   a frame mountable to said base;
   housing means attached to said frame for receiving and housing said plurality of syringes;
   a drive member operative in a direction substantially parallel to the longitudinal axes of said plurality of syringes;
   a plurality of couplings, each of which independently engages one of said plurality of syringes;
   means for releasably securing each of said plurality of couplings to said drive member with an adjustable force so as to halt actuation of at least one of said plurality of syringes should the at least one syringe become inoperative; and
   platform means attached to said base for receiving and supporting said thin layer chromatography plate.

2. The apparatus of claim 1 wherein said frame includes a groove for guiding said drive member during operation.

3. The apparatus of claim 2 wherein said drive member includes at least one flange for cooperative engagement with said groove in said frame.

4. The apparatus of claim 1 wherein each of said plurality of couplings comprises:
   a body cooperating with said means for releasably securing each of said plurality of couplings; and
   an attachment member pivotably connected to said body for releasably engaging a plunger of one of said plurality of syringes.

5. The apparatus of claim 4 wherein said drive member includes a plurality of apertures disposed substantially perpendicular to the longitudinal axes of said plurality of syringes and wherein each of said means for releasably securing said plurality of couplings comprises:
   a member disposed substantially within said aperture having a portion protruding therefrom for contacting the body of one of said plurality of couplings;
   means for retaining said member substantially within said aperture; and
   means for exerting an adjustable force on said member.

6. The apparatus of claim 4 wherein said drive member includes a plurality of at least partially threaded apertures disposed substantially perpendicular to the longitudinal axes of said plurality of syringes and wherein each of said means for releasably securing said plurality of couplings comprises:
   a spherical member disposed substantially within said aperture having a portion protruding therefrom for contacting the body of one of said plurality of couplings;

means for retaining said spherical member substantially within said aperture;

a spring disposed within said aperture in contact with said spherical member so as to exert a force on said spherical member; and a set screw threadingly engaged with said at least partially threaded aperture for adjusting said force.

7. The apparatus of claim 4 wherein said base includes a first plurality of spaced co-linear indentations and wherein said frame includes means for engaging at least one of said collinear indentations such that said frame may be positioned relative to said base to accommodate various sizes of said plurality of syringes.

8. The apparatus of claim 7 wherein said base includes a second plurality of spaced co-linear indentations positioned parallel to said first plurality of spaced co-linear indentations so as to accommodate lateral positioning of said frame relative to said base.

9. The apparatus of claim 4 further comprising means for inclining said frame relative to said base so as to adjust an angle formed therebetween.

10. The apparatus of claim 9 wherein said angle is within the range of about 0 to 45 degrees.

* * * * *